US011207078B2

(12) United States Patent
Purdy et al.

(10) Patent No.: US 11,207,078 B2
(45) Date of Patent: Dec. 28, 2021

(54) ORTHOPEDIC REAMER FOR BONE PREPARATION, PARTICULARLY GLENOID PREPARATION

(71) Applicant: Tornier SAS, Montbonnot Saint Martin (FR)

(72) Inventors: Matthew J. Purdy, Winona Lake, IN (US); Lucile Ferrand, Montbonnot (FR); Pierric Deransart, Saint Martin d'uriage (FR)

(73) Assignee: TORNIER SAS, Montbonnot Saint Martin (FR)

( * ) Notice: Subject to any disclaimer, the term of this patent is extended or adjusted under 35 U.S.C. 154(b) by 243 days.

(21) Appl. No.: 16/395,968

(22) Filed: Apr. 26, 2019

(65) Prior Publication Data
US 2019/0247056 A1     Aug. 15, 2019

Related U.S. Application Data

(63) Continuation of application No. 13/291,855, filed on Nov. 8, 2011, now Pat. No. 10,314,596.
(Continued)

(30) Foreign Application Priority Data

Nov. 10, 2010 (FR) ........................... 1059302

(51) Int. Cl.
*A61B 17/16* (2006.01)

(52) U.S. Cl.
CPC ...... *A61B 17/1615* (2013.01); *A61B 17/1684* (2013.01); *A61B 17/1697* (2013.01); *A61B 17/1617* (2013.01); *A61B 17/1659* (2013.01)

(58) Field of Classification Search
CPC ........... A61B 17/1684; A61B 17/1697; A61B 17/1614; A61B 17/1617; A61B 17/1778;
(Continued)

(56) References Cited

U.S. PATENT DOCUMENTS

| 3,559,514 A | 2/1971 | Brownfield |
| 5,203,653 A | 4/1993 | Kudla |

(Continued)

FOREIGN PATENT DOCUMENTS

| DE | 69825973 T2 | 9/2005 |
| EP | 1752105 B1 | 7/2008 |

(Continued)

OTHER PUBLICATIONS

Tornier. (2008). Affiniti Glenoid [Brochure], Author. Retrieved Feb. 19, 2021, from http://faculty.washington.edu/alexbert/Shoulder/Surgery/TornierAffinititechnique.pdf.) (Year: 2008).*
(Continued)

*Primary Examiner* — Marcela I. Shirsat
(74) *Attorney, Agent, or Firm* — Duane Morris LLP

(57) ABSTRACT

Embodiments of the invention include an orthopedic milling machine for preparing a glenoid bone. The milling machine uses a hub and a sleeve. The hub includes reliefs arranged to cut or mill the bone and the sleeve couples to the hub to transfer rotational motion to the hub. The hub has an axial bore sized to receive an orthopedic guide pin. The hub also has a lateral passage slot that allows the hub to move laterally towards the guide pin in order to place the guide pin within the axial bore.

9 Claims, 8 Drawing Sheets

Related U.S. Application Data

(60) Provisional application No. 61/411,429, filed on Nov. 8, 2010.

(58) Field of Classification Search
CPC ............ A61B 17/1659; A61B 17/1615; A61B 17/1666; A61B 2017/00238; A61B 2017/1602; A61F 2002/4631; A61F 2/4801; A61F 2/40; Y10T 408/8953; Y10T 408/895
USPC ........ 606/79–81, 83–85, 167, 170–171, 180; 175/377
See application file for complete search history.

(56) References Cited

U.S. PATENT DOCUMENTS

| | | |
|---|---|---|
| 5,591,170 A | 1/1997 | Spievack et al. |
| 5,800,551 A | 9/1998 | Williamson et al. |
| 5,919,195 A | 7/1999 | Wilson et al. |
| 6,699,289 B2 | 3/2004 | Iannotti et al. |
| 6,949,101 B2 | 9/2005 | McCleary et al. |
| 7,217,271 B2 | 5/2007 | Wolford et al. |
| 7,473,254 B2 | 1/2009 | White et al. |
| 7,503,921 B2 | 3/2009 | Berthusen et al. |
| 7,572,259 B2 | 8/2009 | Desarzens et al. |
| 7,637,909 B2 | 12/2009 | Lechot et al. |
| 7,749,227 B2 | 7/2010 | Lechot et al. |
| 7,780,669 B2 | 8/2010 | Lechot et al. |
| 7,785,329 B2 | 8/2010 | Lechot et al. |
| 7,803,160 B2 | 9/2010 | Keller |
| 7,819,875 B2 | 10/2010 | Chana |
| 7,892,287 B2 | 2/2011 | Deffenbaugh |
| 7,922,769 B2 | 4/2011 | Deffenbaugh et al. |
| 7,927,335 B2 | 4/2011 | Deffenbaugh et al. |
| 8,052,690 B2 | 11/2011 | Berthusen et al. |
| 8,282,639 B2 | 10/2012 | Chana |
| 8,475,460 B1 | 7/2013 | Roger et al. |
| 8,480,674 B1 | 7/2013 | Roger et al. |
| 8,486,076 B2 | 7/2013 | Chavarria |
| 8,657,833 B2 | 2/2014 | Burgi et al. |
| 8,657,834 B2 | 2/2014 | Burgi et al. |
| 8,721,727 B2 | 5/2014 | Ratron et al. |
| 8,740,907 B2 | 6/2014 | Penenberg |
| 8,771,275 B2 | 7/2014 | Xie et al. |
| 8,834,471 B2 | 9/2014 | Roger et al. |
| 8,864,834 B2 | 10/2014 | Boileau et al. |
| 9,066,730 B2 | 6/2015 | McMinn et al. |
| 9,066,731 B2 | 6/2015 | Moore |
| 9,078,672 B1 | 7/2015 | Rossé |
| 9,408,652 B2 | 8/2016 | Hassler et al. |
| 9,814,471 B2 | 11/2017 | Goldberg et al. |
| 10,028,838 B2 | 7/2018 | Hodorek et al. |
| 10,314,596 B2 | 6/2019 | Purdy et al. |
| 2003/0163135 A1 | 8/2003 | Hathaway |
| 2003/0220646 A1 | 11/2003 | Thelen et al. |
| 2004/0097947 A1 | 5/2004 | Wolford et al. |
| 2004/0236339 A1* | 11/2004 | Pepper ................. A61B 17/164 606/80 |
| 2005/0159751 A1 | 7/2005 | Berthusen et al. |
| 2006/0015110 A1 | 1/2006 | Pepper |
| 2006/0058809 A1 | 3/2006 | Zink et al. |
| 2007/0038302 A1 | 2/2007 | Shultz et al. |
| 2007/0038303 A1 | 2/2007 | Myerson et al. |
| 2007/0093840 A1 | 4/2007 | Pacelli et al. |
| 2007/0276393 A1 | 11/2007 | Bonadei |
| 2009/0270863 A1 | 10/2009 | Maisonneuve |
| 2010/0228352 A1 | 9/2010 | Courtney, Jr. |
| 2011/0004215 A1 | 1/2011 | Bradley et al. |
| 2011/0028977 A1 | 2/2011 | Rauscher et al. |
| 2012/0109229 A1 | 5/2012 | Forsell |
| 2012/0123419 A1 | 5/2012 | Purdy et al. |
| 2012/0239042 A1 | 9/2012 | Lappin et al. |
| 2013/0144393 A1 | 6/2013 | Mutchler et al. |
| 2016/0310285 A1 | 10/2016 | Kovacs et al. |
| 2020/0000601 A1 | 1/2020 | Hodorek et al. |

FOREIGN PATENT DOCUMENTS

| | | |
|---|---|---|
| EP | 2231032 B1 | 8/2011 |
| EP | 2363098 B1 | 9/2012 |
| EP | 2626017 A1 | 8/2013 |
| GB | 2406278 A | 3/2005 |
| WO | WO 2005/094693 | 10/2005 |
| WO | WO 2009/083707 | 7/2009 |
| WO | WO 2011/012318 | 2/2011 |
| WO | WO 2014/063197 | 5/2014 |

OTHER PUBLICATIONS

"Assembly/Disassembly Instructions," Product: CMI Reamer, Tornier, Inc., available as early as Jan. 2013, pp. 1-2.

"Global Enable Glenoid Exposure Simplified—Design Rationale and Surgical Technique." DePuy Orthopaedics, Inc., 2010. pp. 1-24.

European Search Report and issued in EP Appl. No. 11188050.6 dated Dec. 7, 2011 in 4 pages.

French Search Report issued in FR Application No. FR 1059302, 4 pages.

"Global STEPTECH Anchor Peg Glenoid Surgical Technique," DePuy Orthopaedics, Inc., Mar. 2014, pp. 1-32.

Notice of Opposition in EP Application No. 11188050.6 dated Mar. 1, 2017 in 6 pages.

DePuy Synthes. "Global APG + Anchor Peg Glenoid—Design Rationale and Surgical Technique." DePuy Synthes, 2010. Web. Dec. 22, 2014. <http://www.synthes.com/sites/NA/NAContent/Docs/Product Support Materials/Technique Guides/0612-13-509_GlobalAPGdesignrationaleST.pdf>.

Zimmer®. "Trabecular Metal Glenoid—Surgical Technique." 2008, 2009. <http://www.zimmer.com/content/pdf/en-US/Trabecular_Metal_Glenoid_Surgical_Technique_97-4301-204-00_Rev_1_11_2009_US_ONLY.pdf> Last Accessed: May 1, 2014.

* cited by examiner

ORTHOPEDIC REAMER FOR BONE PREPARATION, PARTICULARLY GLENOID PREPARATION

CROSS-REFERENCE TO RELATED APPLICATION

This application is a continuation of U.S. application Ser. No. 13/291,855, filed Nov. 8, 2011, which claims the benefit of U.S. Provisional Application No. 61/411,429, filed Nov. 8, 2010, and claims foreign priority to French Patent Application No. FR 1059302, filed Nov. 10, 2010. These applications are herein incorporated by reference in their entireties.

BACKGROUND

During the implantation of a glenoid component of a shoulder prosthesis, the surgeon must prepare the glenoid of the patient in order to bear and immobilize the glenoid component of the shoulder prosthesis. To that end, the surgeon generally uses a motorized or manual milling machine. The milling machine comprises a burr whose proximal side is secured to a driving grip. The distal surface of the burr has reliefs, such as teeth, blades, and/or tips. The burr rotates or oscillates around its central axis in order to shave the bone material making up the glenoid and hollow, cut into, and/or grate the bone material until the glenoid is given a shape adapted to the prosthetic glenoid component to be implanted. For example, the burr hollows a bowl-shaped cavity in the glenoid in which a dedicated portion of the prosthetic glenoid component is housed in a substantially complementary manner. The bowl-shaped cavity may be a hemisphere or another concave cavity.

Furthermore, one potentially significant parameter for lasting stability of a prosthetic glenoid component relates to the proper positioning of that component on the glenoid. Thus, during surgical operations aiming to implant a glenoid component, an orthopedic guide pin, which may be a rod, is pushed partially into the glenoid at a predetermined point and in a predetermined direction. In that manner, the longitudinal part of said rod protrudes from the glenoid and may be used by the surgeon to guide and manipulate different ancillaries. For example, particular bone preparation ancillaries for the glenoid are axially engaged around the guide pin and then slid along said pin.

In particular, the surgeon has milling machines, like those mentioned above, in which the burr includes a hub with a central through bore that is dimensioned to axially receive the guide pin. During a surgical operation, after having placed the guide pin, the surgeon axially slips the proximal end of the pin into the central bore of the burr and then slides said burr and its proximal sleeve along the guide pin towards the glenoid until the distal surface of the burr is pressed against the glenoid. Burrs with a central hub may also be referred to as "cannulated burrs." By rotating or oscillating the burr around the guide pin, the glenoid is milled precisely, in that the milling is well positioned relative to the glenoid due to the cooperation between the central hub of the burr and the guide pin.

However, the use of cannulated burrs poses implementation difficulties related to the presence of soft tissues around the glenoid as well as the proximity of the humeral head of the operated patient. It is therefore often necessary to place spacers to widely expose the glenoid in order to bring the glenoid longitudinally closer to the pin and avoid interference between the soft tissues and the burrs slid along the guide pin towards the glenoid. It is also often necessary to greatly displace the humeral head, or even resect the humeral head. In some cases, this procedure has the possibility of resulting in trauma and scars that may be significant for the patient.

SUMMARY

Embodiments of the present invention relate to an orthopedic milling machine for bone preparation, in particular glenoid preparation, and to a surgical method for preparing a bone, in particular a glenoid, by milling the bone using a milling machine.

Some embodiments of the present invention include an orthopedic burr that is easier for the surgeon to use and that is less traumatic for the patient. Specifically, those embodiments relate to an orthopedic milling machine for bone preparation, in particular glenoid preparation, having a burr that includes a hub. The hub includes an axial bore for receiving an orthopedic guide pin and the hub delimits a lateral passage slot for the guide pin. The slot emerges substantially radially from the bore through the hub.

Embodiments of the present invention also relate to a surgical method for preparing a bone, in particular a glenoid, by milling, wherein:
  a bone to be milled is exposed,
  an orthopedic guide pin is placed in the bone,
  a burr is positioned near the guide pin, the burr including a hub provided with a bore that can receive the guide pin and that delimits a lateral passage slot for the guide pin, the slot emerging substantially radially from the bore,
  the burr is brought laterally closer to the guide pin so that the guide pin is engaged radially through the slot until it reaches the inside of the bore, and
  the burr is driven around the pin to mill the bone.

In those embodiments, the burr is brought laterally closer to the orthopedic guide pin, so as to bring the burr opposite a bone to be milled. Specifically, the burr is not brought frontally relative to said bone, but instead approaches laterally thereto. In this way, in the case of a glenoid milling machine, the burr can be slid or inserted between the patient's humeral head and shoulder blade until the burr is centered with the guide pin, without having to distract the patient's shoulder too greatly, or without having to move the soft tissues surrounding the glenoid away over the entire periphery thereof. To achieve such centering, the guide pin passes radially through the wall of the hub, which is made possible according to some embodiments by engaging the guide pin through a slot of the hub, dimensioned to that end. Thus, the burr may be placed on the bone, in particular on the glenoid, in a simplified and minimally invasive manner while still being able to mill the bone precisely using the burr and the guide pin. In practice, the actuation of the burr, for example rotating or oscillating the burr around the axis of its hub, can either be motorized or manual; in both cases, the hub of the burr can be coupled to an ad hoc driving mechanism that is slid axially around the guide pin.

Releasing the burr according to embodiments of the invention may be done just as easily, by moving it laterally to the glenoid so as to disengage its hub from the guide pin, via the slot of the hub.

Some embodiments include additional features that may be used individually or in combination, such as:
  the burr includes a milling body, which is provided with bone etching reliefs and which extends transversely to the hub and outwardly surrounds the periphery of the hub at least in part, while leaving the opening of the slot open, radially opposite the bore;

the milling body extends all around the hub and includes both a crown, radially distant from the hub, and lugs that connect the hub and the crown in a substantially radial direction and that are distributed around the hub;

the slot extends, radially opposite the bore, in a free volume delimited between two consecutive lugs around the hub;

the crown delimits a lateral passage for the guide pin, said passage connecting said free volume and the outer peripheral surface of the crown;

the passage and the slot are situated substantially aligned in a direction radial to the axis of the hub;

the edges of the passage are inclined by at least 30° relative to a direction radial to axis X-X of the hub;

the crown is uninterrupted around the entire periphery thereof;

one of the lugs delimits an opening for laterally receiving the guide pin, said opening connecting the outer peripheral surface of the crown and the slot;

the milling body extends over only a peripheral portion of the hub, outside of which the slot is situated; and/or the milling machine also includes mechanisms for driving the burr, which are adapted to be simultaneously engaged around the guide pin and coupled to the hub in order to drive the burr around the axis of its hub.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
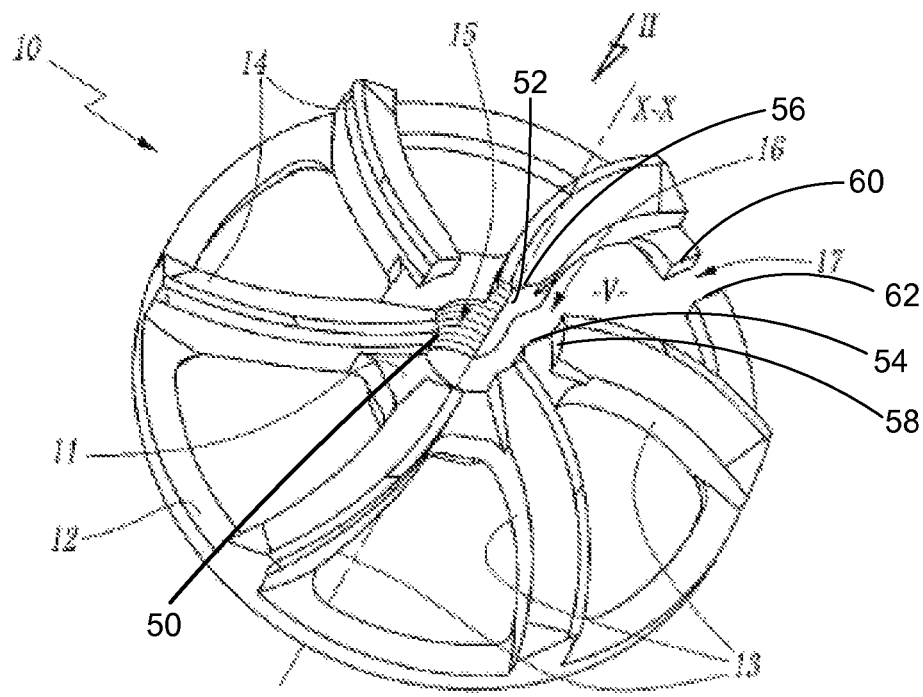
FIG. 1 is a perspective view of a first embodiment of a burr of a milling machine.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
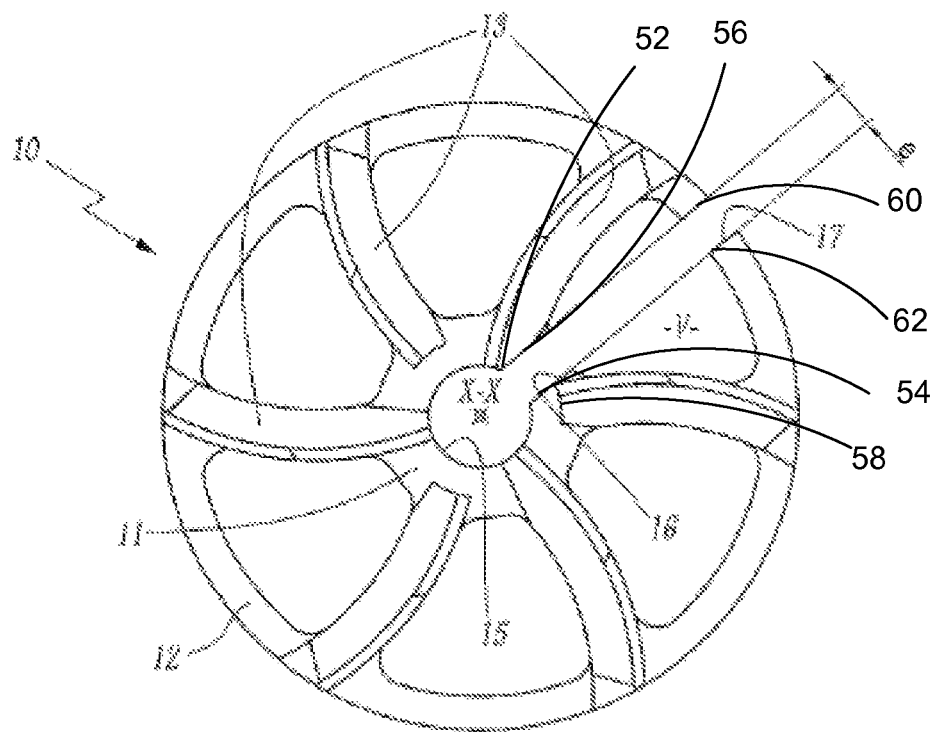
FIG. 2 is an elevation view along arrow II of FIG. 1.
Figure 3:
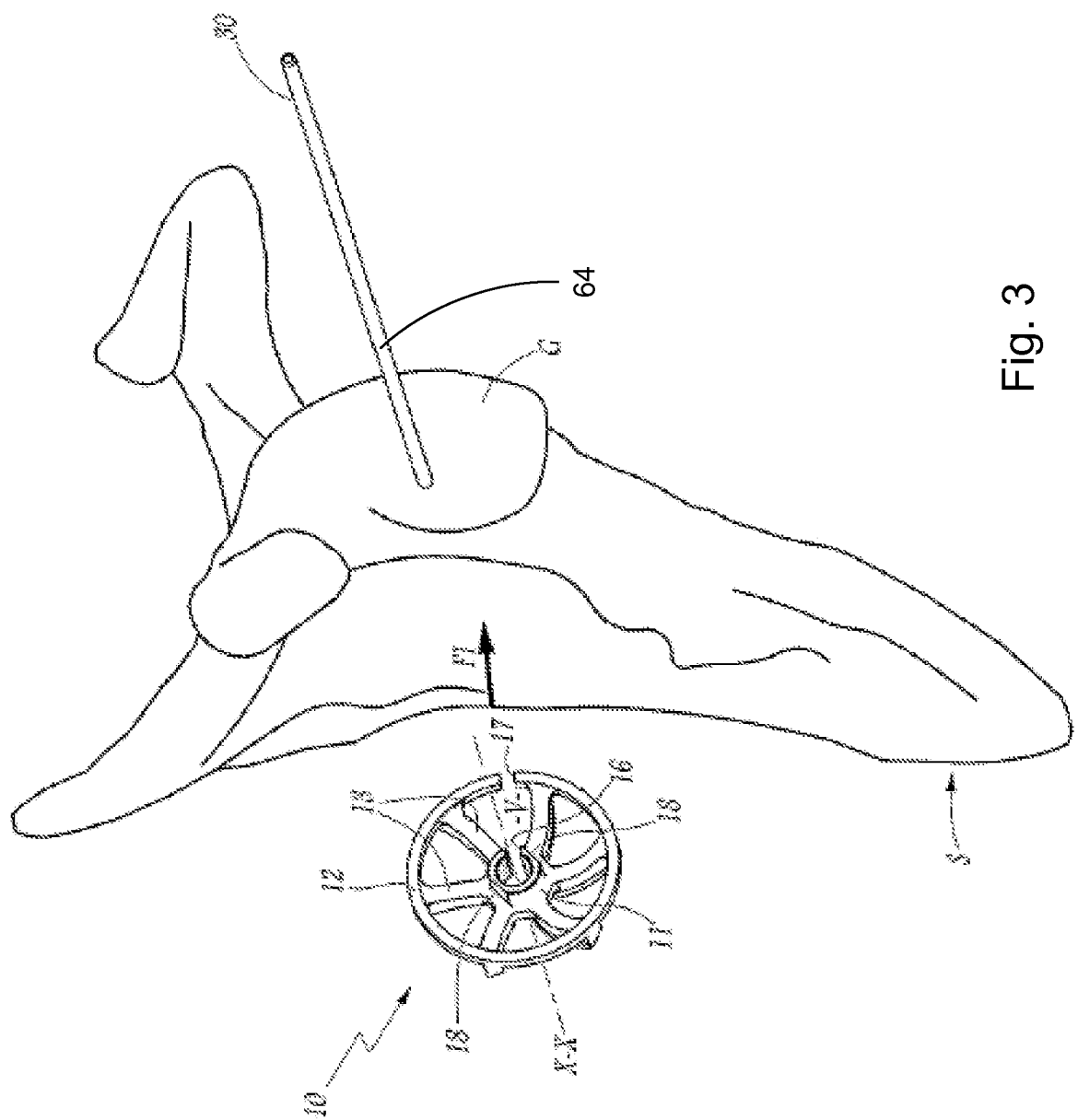
FIG. 3 is a perspective view of the burr of FIGS. 1 and 2, along with a glenoid to be milled and a guide pin placed in the glenoid.
Figure 4:
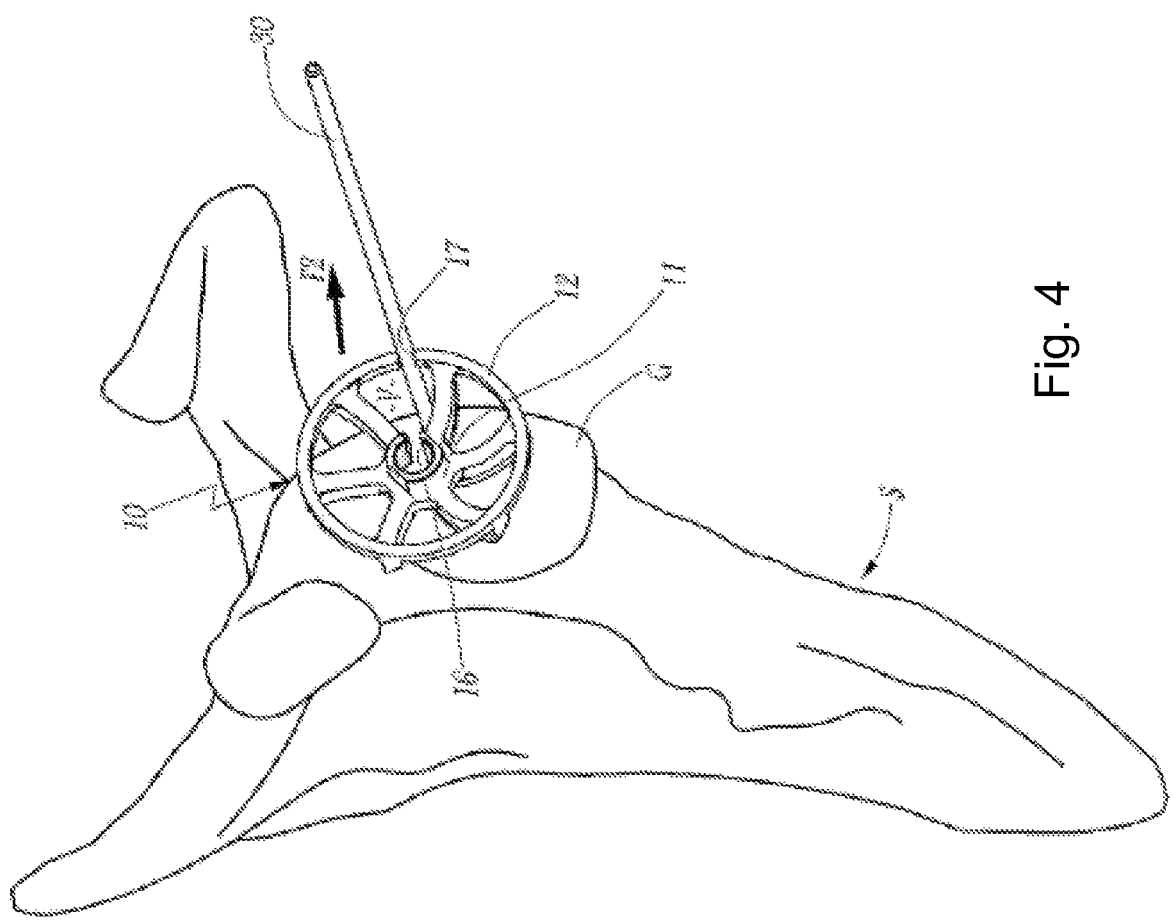
FIG. 4 is a perspective view of the burr of FIGS. 1 and 2, along with a glenoid to be milled and a guide pin placed in the glenoid, in which the guide pin passes through a passage in the burr.
Figure 5:
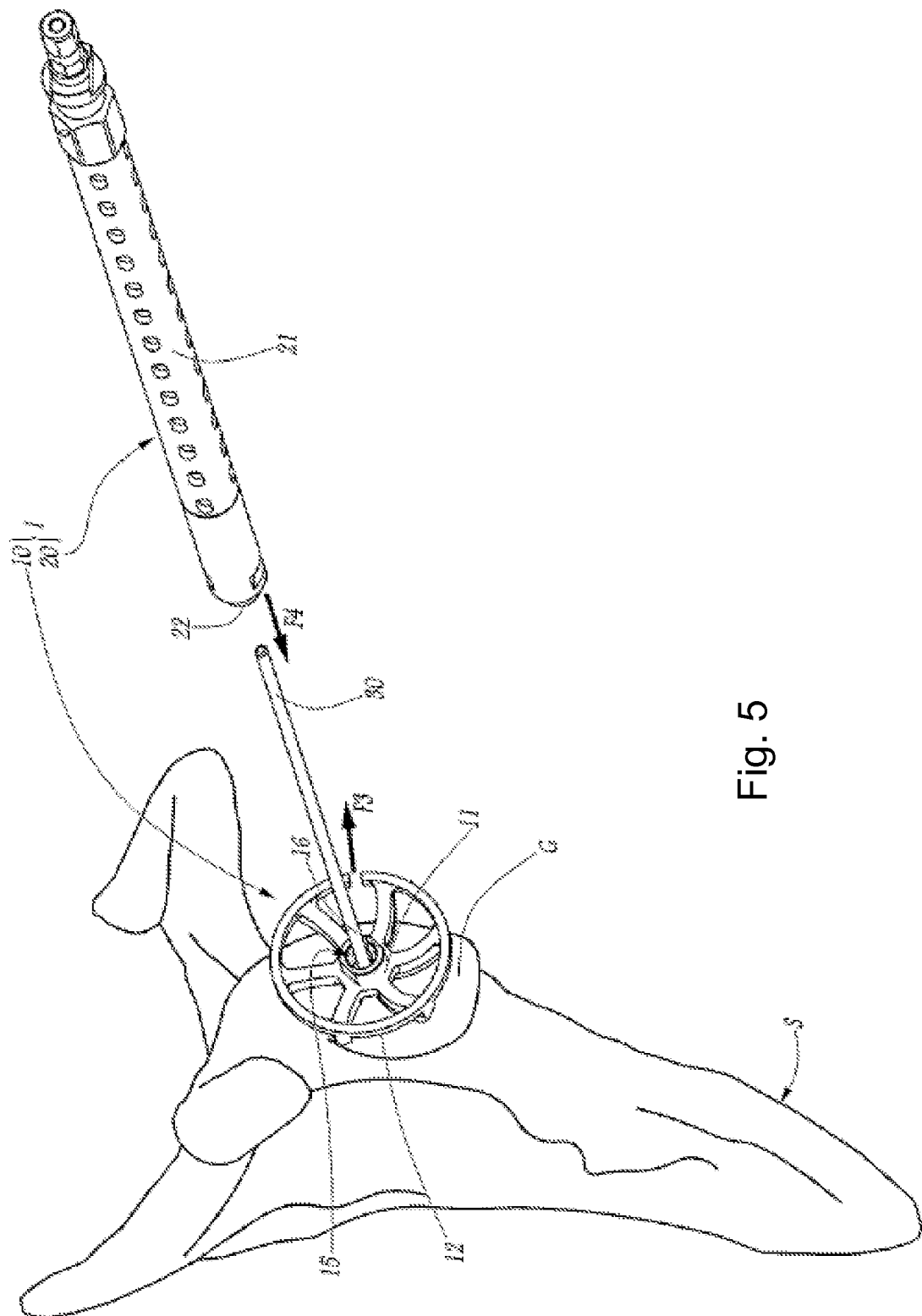
FIG. 5 is a perspective view of the burr of FIGS. 1 and 2, along with a glenoid to be milled, a guide pin, and a sleeve, in which the guide pin resides in a bore in the burr and the sleeve is placed over the guide pin.
Figure 6:
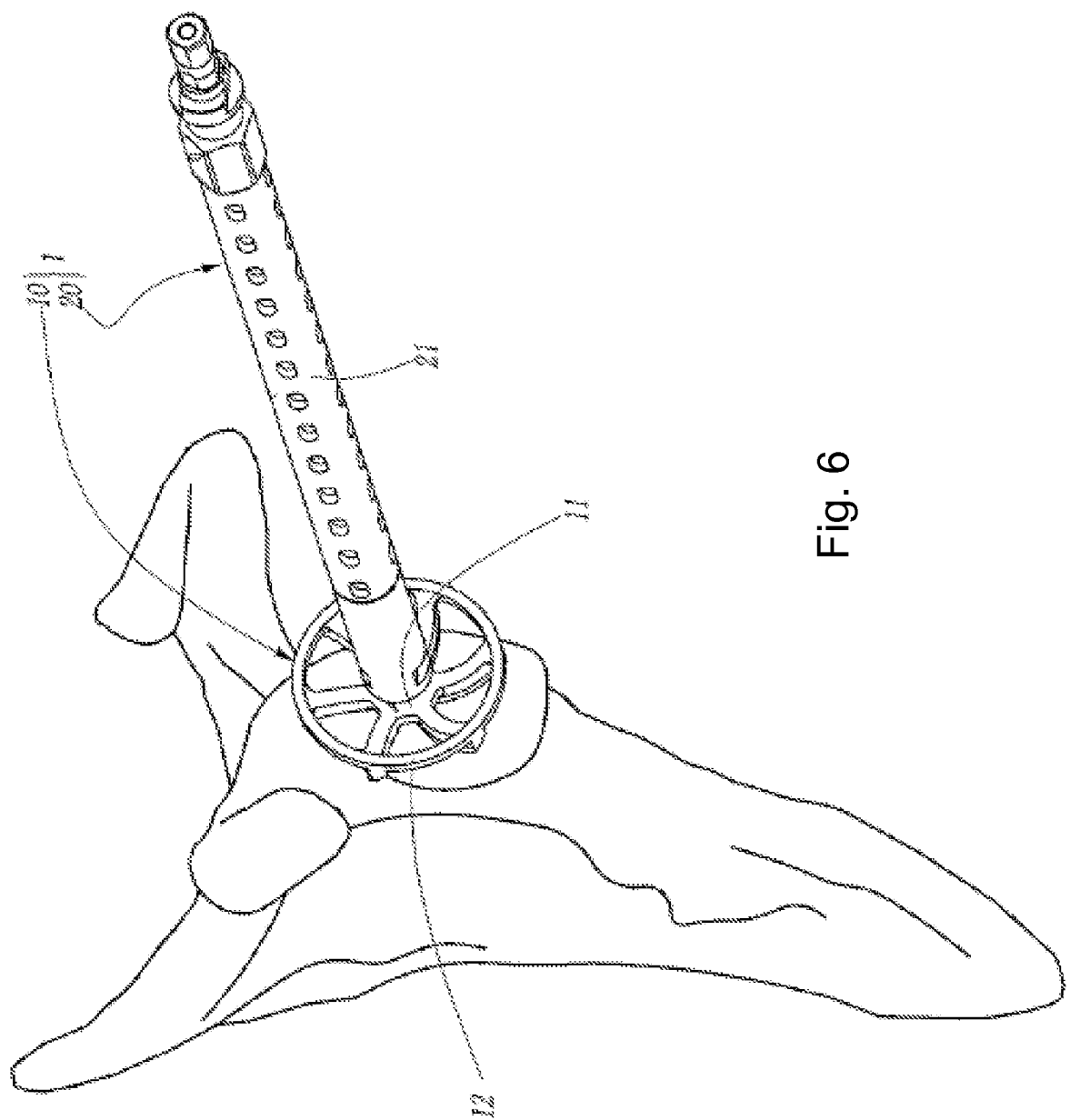
FIG. 6 is a perspective view of the burr of FIGS. 1 and 2, along with a glenoid to be milled and a sleeve, in which the sleeve is coupled to the burr.

FIGS. 1 to 6 show embodiments of a milling machine 1 that include a burr 10, shown alone in FIGS. 1 and 2, and mechanism 20 for driving the burr 10, shown in FIGS. 5 and 6. The mechanism 20 for driving the burr may include a sleeve 21, which is described in more detail below, in light of FIGS. 5 and 6.

According to the embodiments shown in FIGS. 1 to 3, the burr 10 has a discoid shape with a circular base, centered on an axis X-X. More specifically, the burr 10 includes two concentric annular portions, e.g. an inner hub 11 and an outer crown 12, both centered on axis X-X. The hub 11 and the crown 12 are rigidly connected to one another by six individually identical lugs 13, which each extend lengthwise from the hub 11 in a direction substantially radial to axis X-X and which are distributed substantially uniformly around the hub. These lugs 13 need not be strictly rectilinear, but may have a slight, lengthwise curve. The lugs 13 may have longitudinal profiles of various shapes and sizes, and the embodiments described below are non-limiting examples.

On their distal surface, e.g., the surface facing the reader looking at FIGS. 1 and 2, the lugs 13 are each provided with a blade 14 that runs over the entire length of the lug 13. The blades 14 are designed to etch the bone matter and thus to mill the bone matter when the burr 10 is rotated around its axis X-X. To that end, each blade 14 is, for example, provided with a cutting edge extending over the distal end rim of the corresponding lug 13. In some embodiments, each of the blades 14 do not extend strictly in a plane perpendicular to axis X-X but are curved to match a spherical enclosure that is curved towards the distal side of the burr 10 and the axis X-X. In other words, each lug 13 will arch up and away from the crown 12 towards the axis X-X with a specific curvature that may substantially correspond to the curvature of a sphere. In this way, when the burr 10 is rotated around axis X-X, the blades 14 are able to hollow out a bowl-shaped cavity in the bone matter when revolving around the axis X-X. In some embodiments, the bowl-shaped cavity is a hemisphere or another concave cavity.

Bone etching reliefs may include components other than the blades 14, such as spurs, teeth, tips, and the like. Furthermore, by way of one alternative not illustrated, such bone etching reliefs can be provided on all or part of the distal surface of the crown 12, as well as on all or part of the distal surface of the hub 11. In other words, more generally, the crown 12 and the lugs 13 form, at least in part, a milling body that is arranged coaxially and transversely to the hub 11 and that can assume various forms.

Given its angular shape, the hub 11 inwardly delimits a bore 15 that is centered on the axis X-X and passes axially all the way through the hub 11, thereby emerging on the distal surface of the hub 11, as shown in FIGS. 1 and 2, and on the proximal surface of the hub 11, as shown in FIG. 3. As described below, the bore 15 may be inwardly tapped so as to accept a threadable connection with a driver.

As shown in FIGS. 1 to 3, the annular wall 50 of the hub 11, which delimits the bore 15, is slotted over its entire axial dimension in only a portion of its periphery, according to embodiments of the present invention. In other words, the annular wall 50 of the hub 11 delimits a transverse slot 16 that connects the distal and proximal surfaces of the hub 11 in the direction of axis X-X and that connects the bore 15 and the outer peripheral surface of the hub 11, for example in a direction radial to axis X-X. In a plane perpendicular to axis X-X, the edges 52, 54 of the slot 16 are remote from one another with a spacing denoted e in FIG. 2. In the embodiments illustrated in FIGS. 1 to 3, the edges 52, 54 of the slot 16 form parallel planes that are also substantially parallel to a diametric plane of the burr 10 passing through axis X-X. By way of one alternative embodiment not illustrated, the aforementioned edges 52, 54 of the slot 16 can have a certain curve, in particular with a profile curved in a plane perpendicular to axis X-X, as long as said edges 52, 54 maintain the spacing e between them in a plane perpendicular to axis X-X.

As illustrated in FIGS. 1 to 3, the slot 16 may be formed in a portion of the hub 11 that is situated along the periphery of the hub 11 between two consecutive lugs 13, more specifically between the ends 56, 58 of said consecutive lugs 13, facing axis X-X. In this way, the slot 16 opens radially opposite its opening to the bore 15 into a free volume V of the milling body of the burr 10. The free volume V is delimited by the two aforementioned consecutive lugs 13 and by the peripheral portion of the crown 12 that connects the ends of the aforementioned consecutive lugs 13, opposite axis X-X. Moreover, within in the aforementioned portion of the crown 12 is a transverse passage 17 that passes radially through the crown 12, thereby connecting the free volume V and the outer peripheral surface of the crown 12. This passage 17 is therefore similar to a through slot made radially through the crown 12. For reasons specified below, this passage 17 may be arranged to be substantially aligned with the slot 16 in a direction radial to axis X-X, as shown in FIG. 2.

The opposite edges 60, 62 of the passage 17 are separated from one another in a plane perpendicular to axis X-X, with a relative spacing substantially equal to the spacing e between the edges of the slot 16.

One example of the use of the burr 10 will now be presented in light of FIGS. 3 to 6, in the context of a surgical operation aiming to prepare the glenoid G of a shoulder blade S in order to implant a glenoid component of a shoulder prosthesis.

As shown in FIG. 3, before using the burr 10 an orthopedic guide pin 30 is placed in the glenoid G. That guide pin 30 consists of a rigid rod with a small transverse section that is, on a distal end portion, pushed into the bone material of the glenoid G. In practice, the tip for pushing the pin 30 into the glenoid G, as well as the direction of that pushing relative to the glenoid, are imposed by the surgeon, who places the pin 30 in accordance with a preferred implantation axis of the aforementioned prosthetic glenoid component. In some embodiments, the surgeon will use the guide pin 30 during surgical operation with several surgical ancillaries. The placement of the guide pin 30 is a well-known operation in orthopedic shoulder surgery, and it will not be described here in further detail.

As shown in FIG. 3, the surgeon brings the burr 10 close the glenoid G to be milled, not by sliding the bore 15 axially around the guide pin 30 but by moving the burr 10 laterally to the guide pin 30 following a plane perpendicular and/or askew to said pin. This lateral approach of the guide pin 30 by the burr 10 is indicated by an arrow F1 in FIG. 3. This lateral approach makes it possible to slide the burr 10 between the shoulder blade S and the humeral head associated with said shoulder blade (not shown), while the distal surface of the burr faces the shoulder blade. In this way, it is not necessary for the surgeon to distract the shoulder joint too much, thereby limiting the trauma to that joint.

As visible by comparing FIGS. 3 and 4, the lateral approach to the guide pin 30 by the burr 10 is continued until the crown 12 of the burr 10 comes into the immediate vicinity of the guide pin 30, more specifically the intermediate portion 64 of said guide pin 30, emerging from the glenoid G. The movement of the burr 10 is then continued, as indicated by arrow F2 in FIG. 4, so as to transversely engage the guide pin 30 through the passage 17 in a direction radial to axis X-X.

For the guide pin 30 to be able to pass through the crown 12 via the passage 17, the spacing between the edges 60, 62 of said passage 17 are at least equal to, or slightly larger than the diameter of the guide pin 30, according to embodiments of the present invention. After crossing the passage 17, the guide pin 30 is positioned inside the crown 12, extending axially through the free volume V.

Still while continuing the lateral approach to the guide pin 30 with the burr 10, the surgeon brings the hub 11 closer to the intermediate portion 64 of said guide pin 30, until said intermediate portion 64 of the guide pin 30 is engaged through the slot 16, as indicated by arrow F3 in FIG. 5. According to the same considerations as before regarding the passage 17, it is understood that the spacing e between the edges 52, 54 of the slot 16 is sufficient, compared to the diameter of the pin 30, to allow said guide pin 30 to pass through the wall of the hub 11, via the slot 16, until the guide pin 30 is located inside the bore 15, in particular in a configuration coaxial to said bore 15, as shown in FIG. 5. In other words, in that configuration, the axis X-X of the burr 10 is combined with the central axis of the guide pin 30. Thus, it will be noted that, in return for the lateral approach described above in reference to FIGS. 3 to 5, the burr 10 has been moved until it is coaxial with the guide pin 30 without needing to axially engage said burr 10 from the proximal end of the guide pin 30. This lateral approach allows the surgeon to limit the extent of the surgical incisions in the soft tissue surrounding the glenoid G, in that those soft tissues only need to be incised and spaced apart over about half of the periphery of the glenoid G.

As shown in FIGS. 5 and 6, a tubular sleeve 21 is configured to slide around the guide pin 30 while being axially engaged around said guide pin 30 from the proximal end thereof. The tubular sleeve 21 slides around the guide pin 30, toward the burr 10, as indicated by arrow F4 in FIG. 5. That sliding movement continues until the distal end 22 of the sleeve 21 reaches the burr 10. The distal end 22 of the sleeve 21 is then mechanically coupled to the hub 11. In some embodiments, that coupling is done by screwing the end 21, threaded for that purpose, into the tapping of the bore 15. Other forms of mechanical coupling between the sleeve 21 and the hub 11 can be used in the context of the present invention.

During coupling operations, the surgeon may manipulate the burr 10 by gripping it by the proximal end of the hub 11. For example, as shown in FIG. 5, the proximal end of the hub 11 delimits two diametrically opposite flats 18, shown in FIG. 5, which allow the surgeon to firmly immobilize the burr 10 in rotation around axis X-X, in order to facilitate screwing of the end 22 of the sleeve 21 in the bore 15. Furthermore, these flats 18 can be used by the surgeon, by themselves if necessary, in order to manipulate the burr 10 during all or each of the steps of its placement.

Once the sleeve 21 is secured to the burr 10, as shown in FIG. 6, said sleeve 21 is rotated around its central longitudinal axis, for example by connecting its proximal end to an ad hoc driving motor. The rotational movement imposed on the sleeve 21 is transmitted to the burr 10 such that the blades 14 shave the bone material making up the glenoid G and mill the bone material as mentioned above. Of course, rather than being motorized, the sleeve 21 can be driven manually.

The milling of the glenoid G by the burr 10 is thus guided by the guide pin 30, inasmuch as said guide pin constitutes the application axis of the burr 10 on the glenoid G. Once the milling of the glenoid G is finished, the sleeve 21 is, after separating the sleeve 21 and the hub 11, released by sliding the sleeve 21 along the guide pin 30 toward the proximal end of said pin. The surgeon then releases the burr 10 laterally from the guide pin 30, making the intermediate portion of said guide pin successively pass through the slot 16 and the passage 17, following a lateral movement opposite to that described in reference to FIGS. 3 to 5.

Figure 7:
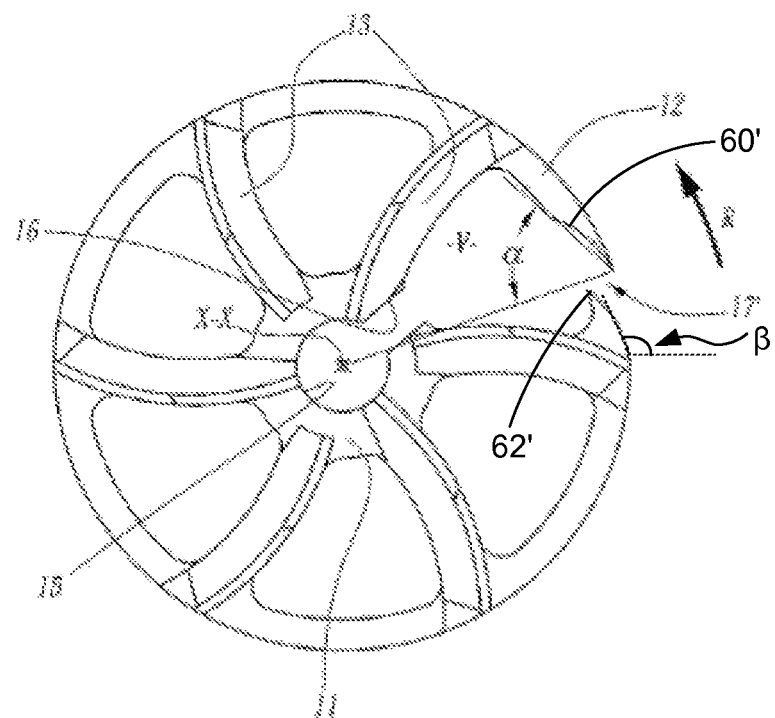
FIG. 7 is an elevation view of a burr according to embodiments of the present invention.

FIG. 7 shows an alternative embodiment of the burr 10, where elements similar to elements in the embodiments shown in FIGS. 1 to 6 bear the same references. This alternative embodiment differs from the embodiment of FIGS. 1 to 6, for example, by the transverse passage provided through the crown 12, said passage being referenced 17' in FIG. 7. More specifically, the passage 17' differs from the passage 17 in that, unlike the passage 17, its edges 60', 62' do not extend in planes parallel to a diametric plane of the burr 10 passing through axis X-X. Instead, those edges 60', 62' of passage 17' are, in a plane perpendicular to said axis X-X, substantially inclined relative to a direction radial to said axis X-X. Thus, in a plane perpendicular to axis X-X, the line connecting the inner and outer ends of each of the edges 60', 62' of the passage 17' form, with a direction radial to axis X-X, a non-zero angle $\alpha$ that is greater than or equal to 30°, or even 45°. In this way, the passage 17' does not extend, between its openings on the outside of the crown 12 and on the free volume V, strictly in a direction radial to axis X-X but along a path inclined relative to said radial direction in comparison to the passage 17. Having a passage 17' oriented as shown in FIG. 7 results in less interference or gripping between the opening on the outside of the passage 17' and elements outwardly surrounding the crown 12 when the burr 10 is rotated in the direction indicated by arrow R in FIG. 7, i.e., in the direction opposite the incline $\alpha$ of the passage 17' relative to the direction radial to axis X-X. In fact, the rear edge 62' of the passage 17' forms, with the outer peripheral surface of the crown 12, an obtuse angle $\beta$, greater than or equal to 135°, which pushes elements that would enter the passage 17' during the rotation of the burr 10 toward the outside of passage 17'. Such elements are, for example, the soft tissue surrounding the glenoid G. In other words, with the embodiment of FIG. 7, the risks of the passage 17' gripping or catching the soft tissue surrounding the glenoid during setting in rotation of the burr 10 in direction R are lower, compared to the embodiment of the burr 10 of FIGS. 1 to 6. Advantageously, rather than being strictly planar, the edges 60', 62' of the passage 17' have, in a cutting plane perpendicular to axis X-X, a curved profile that is curved in the direction opposite axis X-X. This reinforces the non-catching effect of the soft tissue that may be present around the crown 12 when the burr 10 is rotated in direction of rotation R.

It will be noted that the incline $\alpha$ of the passage 17' relative to the direction radial to axis X-X means that its opening on the outside is offset, in a peripheral direction of the crown 12, relative to its opening on the free volume V. Consequently, to place the burr 10 on the glenoid G, the burr must be moved in a different manner than the burr described in FIGS. 1 to 6, in which the engagement of the guide pin 30 through the passage 17 and then the slot 16 more simply consists of a substantially rectilinear movement of the burr 10 relative to the guide pin.

Figure 8:
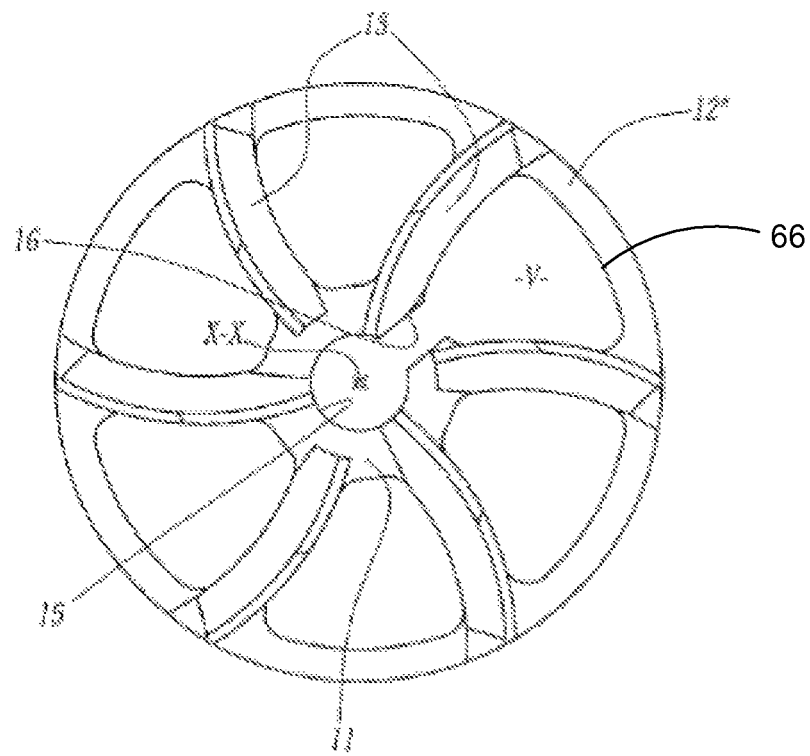
FIG. 8 is an elevation view of a burr according to embodiments of the present invention.

FIG. 8 shows another alternative of the burr 10 of FIGS. 1 to 6, in which the components of the burr that are similar to components in the embodiment of FIGS. 1 to 6 bear the same numerical references. The alternative of FIG. 8 differs from the burr of FIGS. 1 to 6, for example, by the absence of the passage 17. In other words, unlike the crown 12, the crown 12" of the burr 10 of FIG. 8 is uninterrupted over the entire periphery thereof. The absence of passage 17 facilitates the manufacture of the burr 10 but causes a slightly different use from that of the embodiment of FIGS. 1 to 6. For example, inasmuch as the crown 12" is not slotted, it is not possible to bring the guide pin 30 through the free volume V via a lateral approach of said guide pin 30. Also, unlike what was described above in light of FIGS. 3 and 4, the surgeon engages the guide pin 30 axially in the free volume V, e.g., axially engaging the proximal end of said guide pin between the successive lugs 13 delimiting said free volume V. Then, the surgeon slides the burr 10 along the guide pin 10 while the guide pin 30 extends through the free volume V, preferably while the guide pin is pressed laterally against the inner peripheral surface 66 of the crown 12"; in this way, the surgeon brings the burr 10 close to the glenoid G while keeping the burr 10 centric relative to the guide pin 30, preferably as centrically as possible. In so doing, the surgeon can play on the incline of the burr 10 to get around the humeral head, as well as other organs of the patient, while limiting the extent of the incisions and spacing of the soft tissues surrounding the glenoid. Once the burr 10 is slid to the level of the intermediate portion of the guide pin 30 emerging from the glenoid 10, the surgeon brings the hub 11 closer to the guide pin 30 laterally relative thereto, in a similar manner as previously described in light of FIG. 5, so as to engage said intermediate portion of the guide pin 30 through the slot 16 until the bore 15 is made coaxial with the guide pin.

Figure 9:
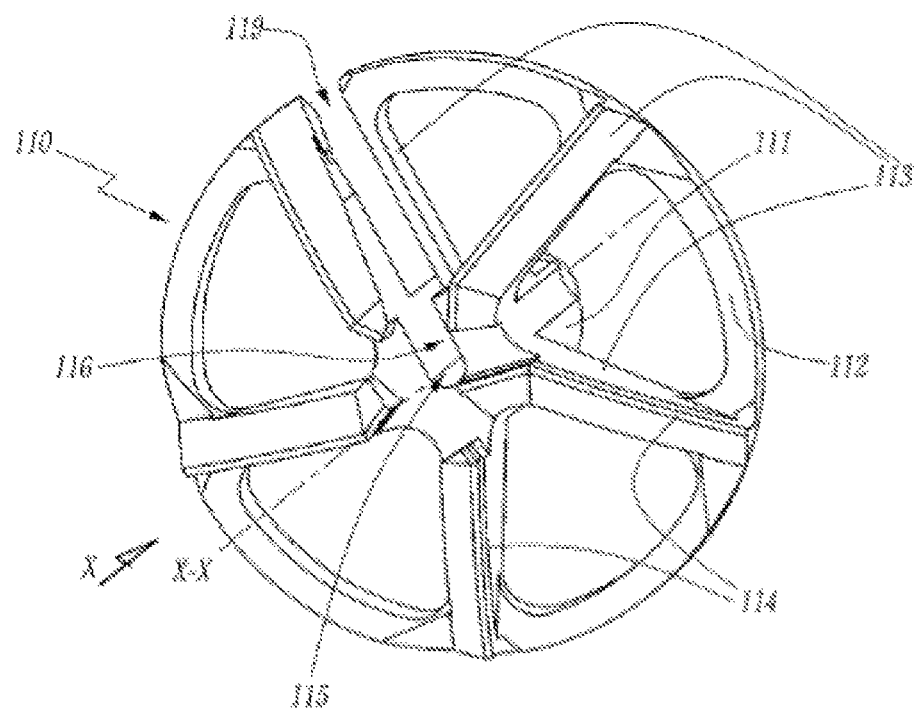
FIG. 9 illustrates a perspective view of a burr according to embodiments of the present invention.
Figure 10:
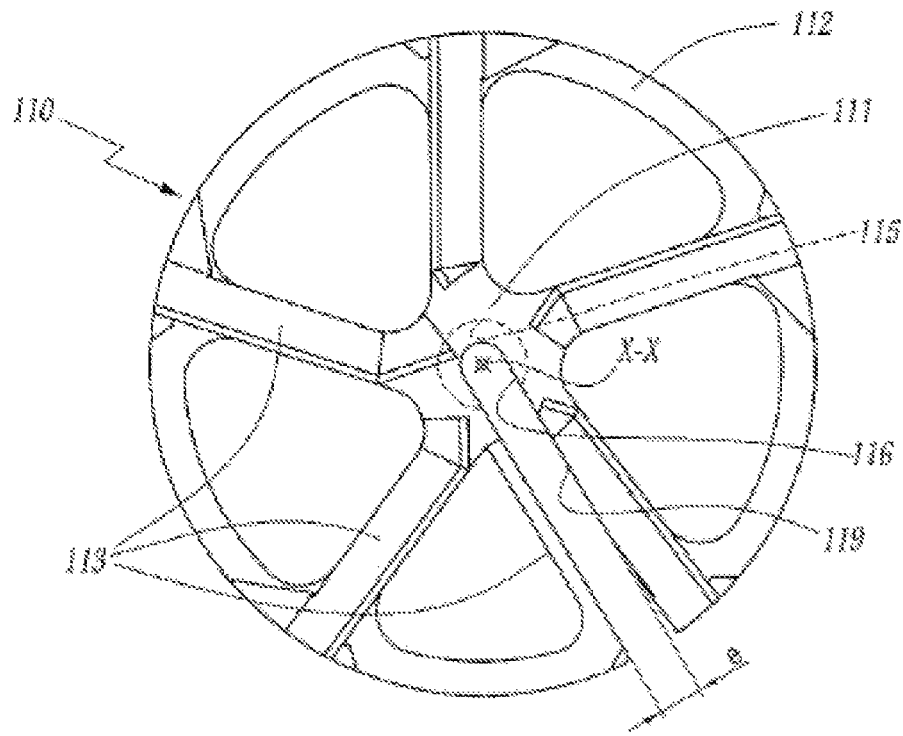
FIG. 10 illustrates an elevation view of the burr of FIG. 9 along arrow X of FIG. 9.

FIGS. 9 and 10 show a burr 110 representing an alternative embodiment of the burr 10. Said burr 110 is in particular designed to be used with the sleeve 21 described above, within a milling machine similar to the milling machine 1.

Similar to the burr 10, the burr 110 includes an inner annular hub 111, which is centered on axis X-X and inwardly delimits a through bore 115, and a milling body that extends transversely around the hub 111. This milling body includes an outer crown 112 and five lugs 113. The lugs 113 connect the hub 111 and the crown 112 in a direction substantially radial to axis X-X and are distributed around that axis along the periphery of the hub 111. Similarly to the lugs 13 of the burr 10, the lugs 113 of the burr 110 include cutting blades 114 on their distal surfaces.

The lugs 113 differ from the lugs 13 in that, in a cutting plane perpendicular to axis X-X, they have a substantially rectilinear profile. Furthermore, unlike the lugs 13 that are all individually identical, the lugs 113 are broken down into a group of four identical lugs 113. The remaining lug 113' differs from the other lugs 113 by the presence of an opening 119 that passes all the way through the lug 113' in the direction of axis X-X, thereby connecting the distal and proximal surfaces of said lug, and running over the entire radial dimension of the lug 113', thereby connecting the inner and outer ends of said lug. More specifically, at the outer end of the aforementioned lug 113', an opening 119 emerges on the outer peripheral surface of the crown 112, while, at the inner end of said lug 113', the opening 119 is extended by a slot 116, functionally similar to the slot 16, delimited through the annular wall of the hub 111. As visible in FIG. 10, in a plane perpendicular to axis X-X, the opening 119 fits into the rectilinear extension of the slot 116, its opposite edges being separated from one another by a space substantially equal to the spacing e between the edges of the slot 116.

The burr 110 is used in substantially the same way as the burr 10: before coupling the hub 111 to the sleeve 21 that slides along the guide pin 30, the burr 110 is brought closer to said guide pin 30 laterally to the intermediate portion thereof, so as to radially engage said intermediate portion of the guide pin 30 through the opening 119 and the slot 116 successively, until reaching the inside the bore 115.

Figure 11:
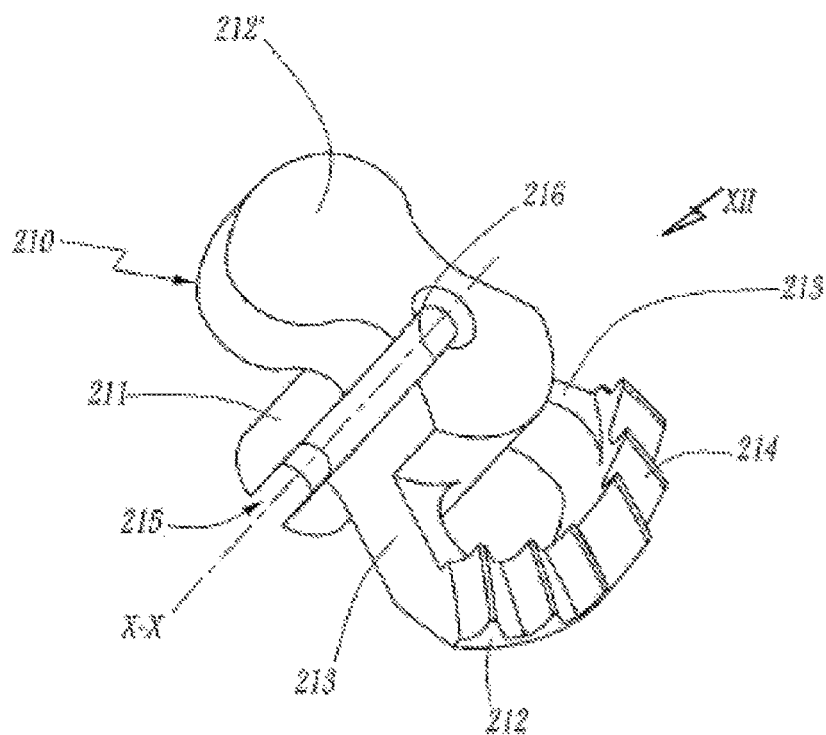
FIG. 11 illustrates a perspective view of a burr according to embodiments of the present invention.
Figure 12:
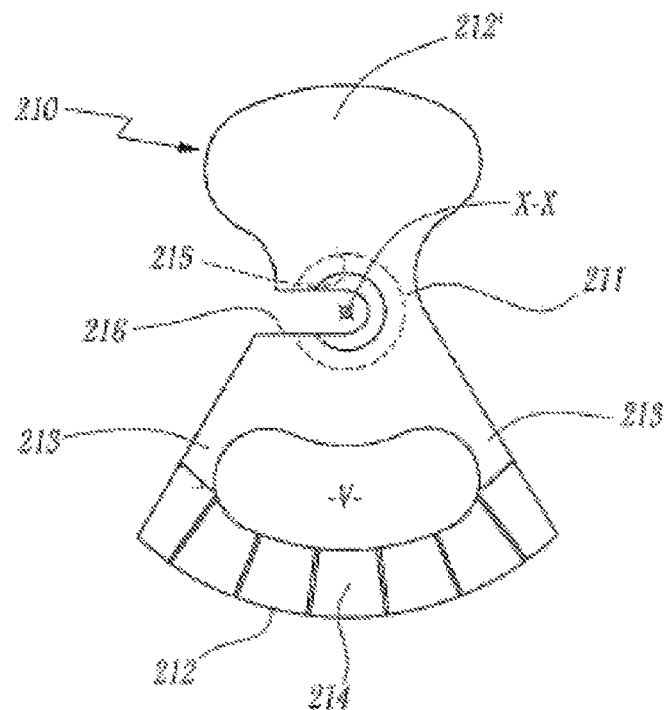
FIG. 12 is an elevation view of the burr of FIG. 11 along arrow XII of FIG. 11.

FIGS. 11 and 12 show an alternative burr 210, according to embodiments of the present invention. In practice, similar to the burrs 10 and 110, the burr 210 is coupled to the sleeve 21 within a milling machine similar to the milling machine 1.

The burr 210 includes an annular hub 211, centered on an axis X-X and functionally similar to the hub 11 or 111 of the burrs 10 or 110.

The bur 210 differs from the burrs 10 and 110, for example, by the overall shape of its milling body; in fact, this body extends over a peripheral portion of the hub 211 and consists of a crown portion 212 connected to the hub 211 by one or more radial lugs 213. On its distal surface, the crown portion 212 is provided with an etching or toothing 214 for milling the glenoid bone matter. In some embodiments, the milling body of the burr 210 has a bulk that is globally much smaller than that of the milling body of the burrs 10 and 110. It is thus understood that the burr 210 may be used to produce bone preparations on a smaller scale.

For balancing reasons, the burr 210 advantageously includes a counterweight 212', which extends transversely from the hub 211 and which is arranged diametrically opposite the crown portion 212.

Similarly to the hub 11 or 111 of the burrs 10 and 110, the hub 211 of the burr 210 simultaneously delimits an inner bore 215, centered on axis X-X, and a lateral slot 216, which connects the inside of the bore 215 and the outside of the hub 211 in a direction radial to axis X-X. As visible in FIG. 12, this slot 216 is situated along the periphery of the hub 211 outside the milling body, i.e., outside the portion delimited by the two lugs 213 in which the crown portion 212 extends. More specifically, in the embodiment shown in FIGS. 11 and 12, the slot 216 extends in a direction radial to axis X-X that is arranged substantially at 90° to the diametric direction in which the crown portion 212 and the counterweight 212' are opposite. As a non-illustrated alternative, the slot 216 can be situated in the same portion as the crown portion 212 and to connect to the free volume V between the two lugs 213.

The use of the burr 210 is similar to that described above for the burrs 10 and 110, in that the placement of the burr 210 on a glenoid to be milled, provided beforehand with the guide pin 30, consists of bringing the burr 210 closer to said guide pin 30 laterally to the intermediate portion of said guide pin 30 so as to radially engage said intermediate portion of the guide pin through the slot 216 until it reaches the inside of the bore 215.

Various arrangements and alternatives to the milling machine described above, in particular the burrs 10, 110 and 210, can also be included alone or in combination, including but not limited to one or more of the following characteristics and/or features:

by way of non-illustrated alternatives for the burrs 10 and 110, their crown 12, 12", or 112 can be eliminated at one or more portions along their periphery, or over the entire periphery thereof, in particular for small burrs;

by way of non-illustrated alternatives for the burr 210, the counterweight 212' can be replaced by a toothed crown portion, symmetrical to the crown portion 212 relative to axis X-X;

rather than having a circular base, the milling body of the burrs 10, 110 and 210 can be centered on axis X-X while having an oval or ovoid or multi-lobed base;

as mentioned above, the geometry of the cavity hollowed out by the burrs 10, 110 and 210 in the bone material is not a necessary limitation of those embodiments; thus, in return for ad hoc arrangements of the distal surface of their milling body, these burrs can perform both a concave spherical activity as described above, or a convex spherical relief, a planar resection, a cavity with a spherical central region and a flat peripheral edge, and the like; and/or embodiments of the invention can be applied to orthopedic milling machines intended to be used on bones other than the glenoid of a shoulder blade; thus, embodiments of the invention are for example applicable to milling the humerus or the bones of the hand or foot.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of preparing a bone, the method comprising:
   sliding a burr between a shoulder blade and a humeral head using a lateral approach until the burr is coaxial with a guide pin previously placed in the shoulder blade without needing to axially engage the burr from a proximal end of the guide pin, the burr including:
   a hub, the burr being configured for rotation about an axis, the hub including a bore adapted to receive a drive shaft; and
   a milling body that extends outwardly and surrounds a periphery of the hub at least in part, the milling body including a crown spaced radially from the hub where the crown is uninterrupted around an entire periphery of the hub and lugs that connect the hub and the crown in a radial direction, the lugs are distributed around the hub, the milling body further including a free volume between two consecutive lugs;
   after sliding the burr between the shoulder blade and the humeral head, coupling the drive shaft with the hub; and
   driving the burr to prepare the bone.

2. The method of claim 1, further comprising:
   advancing the driving shaft axially toward the hub.

3. The method of claim 1, wherein coupling the drive shaft with the hub includes coupling by a threaded connection.

4. The method of claim 1, further comprising milling the bone using bone etching reliefs on a distal surface of the milling body.

5. The method of claim 1, wherein driving the burr defines a concave cavity in the bone.

6. The method of claim 1, further comprising positioning the burr in contact with the shoulder blade using the guide pin.

7. The method of claim 6, further comprising advancing the free volume of the burr toward a bone engaging end of the guide pin.

8. The method of claim 7, wherein the lugs are angled toward the proximal end of the guide pin.

9. The method of claim 1, wherein the hub includes a slot between two of the lugs.

\* \* \* \* \*